United States Patent [19]
Varco

[11] Patent Number: 6,010,690
[45] Date of Patent: Jan. 4, 2000

[54] ALKALINE HAIR CONDITIONING COMPOSITIONS CONTAINING CATIONIC GUAR

[75] Inventor: Joseph J. Varco, Fairfield, Conn.

[73] Assignee: Bristol-Myers Squibb Company, New York, N.Y.

[21] Appl. No.: 09/035,392

[22] Filed: Mar. 5, 1998

[51] Int. Cl.[7] ............................... A61K 7/09; A61K 7/11; A61K 7/06
[52] U.S. Cl. .................................... 424/70.13; 424/70.11; 424/70.5; 424/70.1; 514/880; 132/202; 132/203
[58] Field of Search ............................... 424/70.13, 70.11, 424/70.5, 70.1; 514/880; 132/202, 203

[56] References Cited

U.S. PATENT DOCUMENTS

| 4,387,090 | 6/1983 | Bolich, Jr. . | |
|---|---|---|---|
| 4,557,928 | 12/1985 | Glover . | |
| 5,060,680 | 10/1991 | Akhtar | 132/204 |
| 5,148,822 | 9/1992 | Akhtar | 132/204 |
| 5,217,652 | 6/1993 | Iovanni | 252/547 |
| 5,294,230 | 3/1994 | Wu et al. | 8/127.51 |

FOREIGN PATENT DOCUMENTS

| 702949 | 3/1996 | European Pat. Off. . |
|---|---|---|
| 5345708 | 12/1993 | Japan . |

*Primary Examiner*—Thurman K. Page
*Assistant Examiner*—Brian K. Seidlech
*Attorney, Agent, or Firm*—Morton S. Simon; Charles J. Zeller

[57] ABSTRACT

The invention provides compositions for relaxing and conditioning keratinous fibers, particularly human hair. The compositions of the present invention have a high pH, i.e., a pH greater than 10, preferably, in the range of about 11 to about 14, more preferably about 12 to about 13.5, and include as a conditioning additive a cationic guar. Surprisingly, the cationic guar maintains stability, viscosity and activity over time in the highly alkaline pH of the inventive hair relaxer and conditioning compositions of the present invention. The relaxer compositions of the present invention afford beneficial effects to the user, such as softness and ease of wet combing, and cause less damage to hair following application and use. In addition, the conditioning relaxer compositions of the present invention remain on the hair and provide lasting conditioning and relaxing effects after one or more shampoos.

18 Claims, No Drawings

ALKALINE HAIR CONDITIONING COMPOSITIONS CONTAINING CATIONIC GUAR

FIELD OF THE INVENTION

The present invention relates generally to hair compositions and products which have a high pH and provide a conditioning effect to the hair. More particularly, the invention relates to hair relaxer compositions which are alkaline and contain cationic guar and provide ease of wet combing even after the hair is shampooed. The present invention further embraces other hair products, such as permanent wave or curling formulations, having a high pH and containing cationic guar as a conditioning agent.

BACKGROUND OF THE INVENTION

Hair relaxers are primarily used to loosen and straighten, i.e., "relax", curly, frizzy and kinky hair. Hair relaxers are typically cream products having a high pH (i.e., 12.0 to 14.0) and containing, as active components, strong alkalizing additives, such as sodium hydroxide, lithium hydroxide or calcium hydroxide, to straighten strands of hair. The action of these alkaline additive components results in swelling of the hair to permit penetration of the additives into the cortex of the hair to break chemical bonds and re-form the bonds into a new configuration, thereby relaxing the curling and/or twisting of the hair strands., If the relaxer hair product is combed through the hair during the relaxing process, less curliness and more straightening effects are obtained. Similarly, other alkaline-based hair care products, such as wave and/or curl formulations, that also re-form chemical bonds in the hair to alter the structure of the hair, are commonly used by consumers to change the appearance of the hair. A drawback related to the use of such highly alkaline products is that they can be harsh on the hair; hair may become damaged, dry, rough-feeling and difficult to comb after such relaxer products are applied.

Accordingly, needed in the art are hair compositions and products that serve to condition the hair and have the ability to provide lasting conditioning effects, without harshness, after use of the product and after shampooing. More particularly, hair relaxer compositions are also needed that both straighten and condition the hair, without causing extreme dryness and damage to the hair.

It is a goal in the art to develop hair relaxer compositions comprising one or more relaxing and conditioning components wherein the compositions cause less damage to the hair and do not make it dry and unmanageable. Also needed are hair relaxers which make hair easy to comb and contain ingredients which are stable and have long-lasting effects for the user, even after shampooing. In addition, other hair compositions and treatments, such as wave and/or curl formulations, are needed which not only perform their intended functions on the hair, but which also condition and soften the hair after use, thereby making the treated hair more manageable and causing less damage to the treated hair strands. These and other beneficial results are achieved by the present invention using cationic guars (also described and referred to synonymously heroin as cationic gum derivatives from guar or locust bean gum) to produce novel and gentle hair compositions having high alkaline pH and significant conditioning properties.

European Patent Application No. 702949 discloses cationic modified guar gum as the sole thickening agent in hair dye compositions, but does not disclose or teach cationic guars in hair relaxer compositions having alkaline pH and providing novel and lasting combing and conditioning effects.

Cationic guars are disclosed as additives in particular hair conditioner compositions for use as thickeners, but not as conditioners in line hair relaxer compositions, in Japanese Patent No. 5,345,708, U.S. Pat. No. 4,557,928 and U.S. Pat. No. 4,387,090.

As will be appreciated by those having skill in the pertinent art, commercially-available cationic guar solutions (e.g., Cosmedia; Jaguar®) are generally known to be stable in formulations that have low pH to moderately alkaline pH. In particular, Rhone-Poulenc specifies in its product literature that its quaternized hydroxypropyl guars, sold under the tradename JAGUAR®, should be used in formulations having a pH in the range of 4 to 10 for optimal clarity and stability. Because the guar product literature discloses that guars are unstable at high pH, and thus lose viscosity, one skilled in the art would not be motivated, based on such product literature, to use such guar gums as additives in compositions having high pH. Accordingly, the use and formulation of cationic guars into the highly alkaline hair relaxer/conditioning compositions of the present invention is antithetical to the teachings of the art and to the knowledge of the skilled practitioner. In contrast to the teachings of the prior art, the compositions of the present invention, containing a cationic guar additive at a high pH, surprisingly afford a significant level of stability, viscosity and activity of the cationic guar oiler time.

SUMMARY OF THE INVENTION

It is an object of the present invention to provide compositions for treating keratinous fibers, particularly human hair, wherein the compositions provide their specific properties to the hair and also condition the hair with less damage to the hair after use. In accordance with the present invention, the hair treatment compositions are formulated at high pH (i.e., a pH greater than 10), contain one or more cationic guars and embrace, for example, hair relaxer and high pH wave and/or curl formulations.

It is a further object of the present invention to provide high alkaline hair relaxer/conditioning compositions containing one or more cationic guar additives, wherein the guar is surprisingly stable, viscous and active as a conditioner of the hair, despite the high pH environment of the composition. In accordance with the present invention, the highly alkaline hair relaxer compositions containing cationic guar provide relaxing, conditioning and softening effects for the hair, as well as ease of wet combing, even after shampooing.

It is yet another object of the present invention to formulate a cationic guar as a conditioning additive into a hair treatment or hair care product for combing and conditioning of the hair to achieve extended benefits in wet combing and conditioning and to improve the ease in hair combing compared with. non-guar-containing products. In accordance with the present invention, there is provided a high pH hair system or product containing one or more conditioning cationic guars that leaves the hair soft and manageable and allows for easy comb-out with less damage to the hair from tangles, snarls, knots and the like. The compositions of the present invention are particularly suitable for formulation as hair relaxers and hair waving or curling products, e.g., for producing permanent or semi-permanent waves or curls in the hair.

It is yet another object of the present invention to provide hair care or treatment products for the hair in the form of emulsions or creams, wherein the products are formulations and compositions which are highly alkaline and contain a hair conditioning amount of one or more cationic guars. In accordance with the invention, the conditioning guar will remain stable, viscous and active in the hail product. The products of the present invention have a long shelf life, thereby providing cost benefits and advantages to the consumer.

It will be apparent to those skilled in the art that the compositions of the present invention may be used in conventional permanent wave or curling applications, wherein the advantages afforded by the cationic guar component in relaxer formulations will be similarly apparent in these other applications.

Further objects and advantages afforded by the present invention will be apparent from the detailed description hereinbelow.

DETAILED DESCRIPTION OF THE INVENTION

The present invention provides aqueous hair care and treatment compositions and products comprising a cationic guar (e.g., guar hydroxypropyltrimonium chloride, CTFA nomenclature) as a conditioning additive. As hair relaxers, the compositions of the present invention particularly allow one to achieve relaxation of hair strands coupled with enhanced wet combing effects. The use of cationic guar in the hair compositions of the present invention provides improved hair care products which relax as well as condition and soften the hair.

The cationic guar-containing hair conditioning compositions of the present invention are aqueous-based, highly alkaline, i.e., having a pH greater thin 10, preferably, in the range of about 11 to about 14, more preferably, about 12 to about 13.5, most preferably, about 12.5 to about 13.5. It should be noted that, as used herein, the terms "highly alkaline" and "high pH" are considered to be synonymous.

Prior to the present invention, guar gum solutions were known and reported to be stable at a pH of between about 4 and 10. Moreover, high pH was known and reported to decrease the viscosity of cationic guars. However, the present compositions, containing one or more cationic guars, surprisingly retain and provide conditioning action, and are stable and operative in the high pH environment of the present compositions over time, even though the typical pH range for guar solution stability and viscosity is significantly lower than the pH of the compositions of the present invention. The cationic guar-containing compositions, according to the present invention, provide the consumer with a softening and combing benefit to the hair, while mitigating potential hair damage..

In one embodiment of the present invention, the cationic guar additive has been newly discovered by the present inventor to reduce or eliminate the damaging effects of the relaxer components of the highly alkaline hair relaxer compositions of the present invention. In addition, hair that is treated with the hair relaxer composition in accordance with the present invention retains an ease in wet combing after shampooing and rinsing the relaxer from the hair. Unlike the compositions of the present invention, such a lasting effect is not observed using relaxer compositions that do not contain one or more of the guar additives of this invention.

In contrast to the hair relaxers of the above-described embodiment of the present invention, other active conditioning agents failed to produce the desired effects of conditioning, softness and ease in combing after the hair was shampooed. The other conditioning agents contained amine functional groups and were formulated into hair relaxer compositions at elevated pH, instead of cationic guars, Such unsuitable agents included, for example, dimethicone copolyol amine—Silamine C-300 from Siltech Inc.; polyquaternium 22-copolymer of dimethyl dialkyl ammonium chloride and acrylic acid—Merquat 280 (Calgon); polyquaternium 7, a polymeric quaterneric salt consisting of acrylamide and dimethyl dialkyl ammonium monomers—Merquat 2200 (Calgon); polyquaternium 39, a polymeric quaternary ammonium salt of acrylic acid, diallyl dimethyl ammonium chloride and acrylamide—Merquat Plus 3300 (Calgon); Amodimethicone, Tallowtrimonium Chloride, Nonoxynol-10—Silicone 929 (Dow Corning); trimethylsylamodimethicone—Silicone Q2-8220 (Dow Corning); soytrimonium chloride and isopropanol—Arquad S-50 (Akzo); amodimethiconol, trideceth-12, cetrimonium chloride—2-8739 Microemulsion (Dow Corning); and polyethylenimine copolymer—Lupasol G-20 Waterfree (BASF).

In another embodiment of the present invention, the cationic guar additive has been newly discovered by the present inventor to provide conditioning effects and to reduce or eliminate the damaging effects of other highly alkaline hair products, including those containing components for waving or curling the hair. In addition, hair that is treated with a high pH hair waving or curling composition in accordance with the present invention retains an ease in wet combing after shampooing and rinsing the waving or curling formulation from the hair. Such a lasting effect is not observed using hair waving compositions that do not contain the guar additive, in contrast to the compositions of the present invention.

The improved consumer benefits and effects of the compositions according to the present invention, compared with commercially-available hair relaxer products, have been demonstrated on both laboratory test hair swatches and salon models. The addition of the cationic guar in the relaxer formulation of the present invention permits the relaxation effect to go on unhindered and provides a conditioned feel to the hair after the process has been completed.

The conditioning effect of the compositions of the present invention is even noted with aged (e.g., three months) compositions of the present invention, thus indicating the unexpected chemical stability of the cationic guar additive in combination with the other components, e.g., relaxer components or waving components, of the hair conditioning products of the present invention. Stability testing has demonstrated that the high pH compositions of the present invention which are formulated to include one or more cationic guars remain stable for about three months at 50° C., which is roughly equivalent to a shelf life of about two years at room temperature. In accordance with the present invention, stability of the cationic guar indicates that the cationic guar retains its conditioning effects and remains operative in the compositions over time.

In general, the guar component of the compositions in accordance with the present invention is a cationic derivative of guar gum or locust bean gum. Such gums are polygalactomannans containing two mannose units with a glycoside linkage and a galactose unit attached to one of the hydroxyl groups of the mannose units. The hydroxyl groups are reacted with certain reactive quaternary ammonium compounds to obtain the cationic derivative.

The quaternary ammonium compounds suitable for preparing the cationic gum derivatives of the present invention have the structure

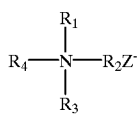

wherein $R_1$, $R_2$ and $R_3$ are alkyl, aryl and substituted alkyl and aryl groups; $R_4$ is, selected from the group consisting of epoxyalkyl and halohydrin, and $Z^-$ is an anion, e.g., $Cl^-$, $Br^-$, $I^-$ and $HSO_4^-$. Suitable epoxyalkyl groups have the structure:

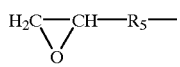

Suitable halohydrins have the structure:

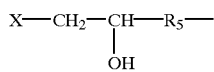

wherein $R_5$ is a divalent alkylene of 1 to 3 carbons, and X is a halogen.

Particularly preferred is the compound 3-(trimethylamino)-2-hydroxypropyl guar chloride which has the structure:

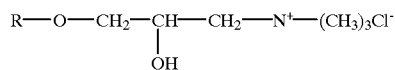

wherein R is the polygalactomannan molecule based on guar, and is sold as Cosmedia Guar 216N by Henkel Corporation.

Particularly preferred for use in the compositions of the present invention are quaternary ammonium derivatives of hydroxypropyl guar, such as guar hydroxypropyltrimonium chloride, which is exemplified by the JAGUAR® products commercially available from Rhone-Poulenc.

In accordance with the present invention, the hair treatment and conditioning compositions as described contain one or more of the above-described cationic gum derivatives in a stable hair conditioning amount. More particularly, the cationic gum derivatives are present in the compositions of the present invention in an amount of from about 0.10% to about 5.0%, preferably, about 0.3% to about 2.0%, more preferably, about 0.50% to about 1.0% by weight, based on the total weight of the composition. It will be appreciated that higher quantities of guar can be used, if more conditioning is required. In such instances, the actual amounts for use can be determined by routine testing.

It is also to be understood that unless otherwise specified herein, all components of the compositions of the present invention are present in % by weight, based on the total weight of the composition.

The compositions of the present invention are generally formulated as emulsions, for example, creams. Gels can also be formulated. Water is generally present in the compositions an amount such as is typically employed in compositions of this type; usually, such amounts are about 40% to 60%, and frequently, about 45% to 50%.

Also formulated in the relaxer and conditioning compositions of the present invention are one or more alkaline earth metal hydroxides, which relax strands of hair. Examples of suitable alkaline earth metal hydroxides include, but are not limited to, sodium hydroxide, calcium hydroxide, lithium hydroxide, potassium hydroxide, barium hydroxide, strontium hydroxide and mixtures thereof. Preferred is sodium hydroxide. Those having skill in the art will appreciate that if calcium hydroxide is used as a relaxer compound, an activator is preferably used, such as guanidine carbonate, as well as others typically known and used in the art. The alkaline earth metal hydroxide is present in the compositions of the present invention at about 1.5% to about 5%, preferably, about 1.9% to about 2.5%.

Secondary or auxiliary conditioning agents in addition to cationic guars can also be formulated into the compositions of the present invention in amounts conventionally used for these reagents. Such auxiliary conditioning agents include those reagents or products which are typically employed in such compositions, nonlimiting examples of which include, but are not limited to, quaternary ammonium compounds, amines, ethyl sulfates and other cationic polymers. Among the quaternary ammonium compounds suitable for use are quaternary ammonium hydroxides, such as methyl triethanol ammonium hydroxide and tetraethyl ammonium hydroxide. Preferred auxiliary conditioning agents include polyquaternium 10 or behentrimonium methosulfate. In general, auxiliary conditioning agents, when used, are present in amounts of about 0.1% to about 3.0%, preferably, about 0.5% to about 2.0%.

The compositions of the present invention may also contain optional ingredients which improve the elegance of the final products, as set forth below. In general, these additional components, and other suitable additives, as desired, provide cosmetically acceptable vehicles for the compositions of the invention and are present at levels which are effective to provide the components' intended functions.

One or more emollients and humectants are generally employed in compositions of this type in amounts typically used in such compositions. Examples of suitable emollients for use in accordance with the present invention include, but are not limited to, mineral oil and petrolatum. Other emollients may include cetyl or stearyl alcohol, paraffin or lanolin alcohol. Emollients are generally employed in the compositions of the present invention at about 5% to about 45%, preferably, about 7.5% to about 40%, by weight. Examples of suitable humectants include, but are not limited to, propylene glycol, hexylene glycol, glycerin and sorbitol. As a general guide, humectants can be present in such compositions in amounts of about 1% to about 20%, preferably, about 4% to about 10%.

One or more emulsifying agents are also generally present in the compositions of this invention in amounts typically employed in such compositions. Emulsifiers typically provide dispersion and suspension of the components, and render a creamy and lubricous consistency to the composition. Nonlimiting examples of emulsifying agents suitable for use include alkoxylated alcohols and fatty alcohols, such as stearyl, cetyl and cetearyl alcohols, ethoxylated sorbitan esters, ethoxylated lanolin and derivatives thereof. As a general guide, emulsifiers can be used in amounts of about 1% to about 16%, preferably, about 2% to about 12%, and more preferably, about 8% to about 10%.

Opacifying agents are conventionally used in cream compositions. Suitable opacifying agents are the higher alcohols, such as stearyl and cetyl alcohol, and the higher acids, such as behenic acid. Sodium chloride and sodium sulfate can also be used as opacifying aids, when used in concentrations that do not cause gelation. Alkaline earth metal fatty acid soaps, such as calcium stearate and magnesium stearate, are also suitable. Magnesium silicates are also useful for this purpose. Opacifying agents are typically present in an amount of from about 0.1%. to about 10%, preferably, from about 0.5% to about 5%.

Thickening agents increase the viscosity of a hair-related product. Suitable materials are natural gums such as tragacenth, xanthan, acacia and locus bean; and synthetic gums such as hydroxypropylcellulose and methyl cellulose. Polyvinyl alcohols can also be used. Alknolamides, "super" amides and the glycol or glycerol stearates may also be used. Thickening agents are present in an amount to provide the desired viscosity. Amounts typically employed are from about 0.1 % to about 10%, preferably, from about 0.1 % to about 10%. The final viscosity of the product should be such that it can be applied to hair and easily distributed therethrough without dripping.

Other optional additives can include antioxidants, such as sodium sulfite; suspending agents; fragrances and herbals; sunscreens; and pH control agents, such as citric acid, each of which is present in an amount, usually less than 5%, effective to provide its intended function. An antidandruff component, e.g., selenium sulfide, may also be included at an effective level.

Relaxer compositions are typically thick heavy creams which, on application, can be easily distributed through the hair without dripping. Accordingly, such compositions usually contain high levels of mineral oil and petrolatum with appropriate emulsifiers. The high oil content of these compositions provide a protective barrier layer on the skin which serves to minimize scalp irritation from the alkalizer component.

EXAMPLES

The following examples as set forth herein are meant to illustrate and exemplify the various aspects of carrying out the present invention and are not intended to limit the invention.

Example 1

A highly alkaline hair relaxer and conditioning composition formulated in accordance with the present invention is presented this example. The final pH of the composition was 13.5.

| INGREDIENTS | % |
| --- | --- |
| Mineral oil | 21.00 |
| Petrolatum | 15.00 |
| Cetearyl alcohol/phosphate ester | 5.00 |
| Stearyl alcohol | 2.00 |
| Cetyl alcohol | 1.00 |
| Ceteareth alcohols | 3.00 |
| Cationic guar | 0.50 |
| Sodium hydroxide | 2.00 |
| Water QS | 100.00 |

Example 2

Another example of a high alkaline hair relaxer and conditioning composition formulated in accordance with the present invention is presented in this example. The final pH of the composition was 13.5.

| INGREDIENTS | % |
| --- | --- |
| Petrolatum | 23.00 |
| Mineral oil | 15.00 |
| Cetearyl alcohol | 5.00 |
| Lanolin derivatives | 2.25 |
| Ethoxylated sorbitan monostearate | 2.64 |
| Cationic guar | 0.50 |
| Propylene glycol | 5.00 |
| Sodium hydroxide | 2.00 |
| Water QS | 100.00 |

Example 3

Another example of a high alkaline hair relaxer and conditioning composition formulated in accordance with the present invention is presented in this example. The final pH of the composition was 12.5.

| INGREDIENTS | % |
| --- | --- |
| Mineral oil | 6.00 |
| Petrolatum | 16.50 |
| Cetearyl alcohol | 8.00 |
| Propylene glycol | 5.00 |
| Calcium hydroxide | 5.00 |
| Cationic guar | 0.50 |
| Water QS | 100.00 |

Example 4

Another example of a high alkaline hair relaxer and conditioning composition formulated in accordance with the present invention is presented in this example. The final pH of the composition was 12.5.

| INGREDIENTS | % |
| --- | --- |
| Mineral oil | 7.00 |
| Petrolatum | 23.00 |
| Silicone fluid | 0.10 |
| Laneth-16/Ethoxylated lanolin | 1.50 |
| Cetearyl alcohol | 5.00 |
| Cationic guar | 0.75 |
| Calcium hydroxide | 5.00 |
| Propylene glycol | 5.00 |
| Water QS | 100.00 |

Example 5

Another example of a high alkaline hair relaxer and conditioning composition formulated in accordance with the present invention is presented in this example. The final pH of the composition was 12.9.

| INGREDIENTS | % |
| --- | --- |
| Petrolatum | 23.00 |
| Mineral oil | 14.00 |
| Laneth-16/Ethoxylated lanolin | 3.00 |
| Cetearyl alcohol | 5.50 |
| Lithium hydroxide | 2.00 |
| Propylene glycol | 5.00 |
| Cationic guar | 2.00 |
| Water QS | 100.00 |

Example 6

Another highly alkaline hair relaxer and conditioning composition formulated in accordance with the present invention is shown in this example. The final pH of the composition was 13.5.

| INGREDIENTS | % |
|---|---|
| Mineral oil | 21.00 |
| Petrolatum | 15.00 |
| Cetearyl alcohol/cetearyl phosphate | 5.00 |
| Stearyl alcohol | 2.00 |
| Cetyl alcohol | 1.00 |
| Steareth-2 | 0.50 |
| Steareth-10 | 2.50 |
| Stearic acid | 0.10 |
| Cationic guar | 0.50 |
| Behentrimonium methosulfate and Cetearylphosphate | 1.00 |
| Propylene glycol | 3.00 |
| Sodium hydroxide | 2.40 |
| Water QS | 100.00 |

Example 7

Another highly alkaline hair relaxer and conditioning composition was formulated in accordance with the present invention as shown in this example. The final pH of the composition was 12.5.

| INGREDIENTS | % |
|---|---|
| Mineral oil | 7.00 |
| Petrolatum | 23.00 |
| Silicone fluid | 0.10 |
| Laneth-16/Ethoxylated lanolin | 1.50 |
| Cetearyl alcohol | 5.00 |
| Cationic guar | 0.75 |
| Polyquaternium 10 | 0.50 |
| Calcium hydroxide | 5.00 |
| Propylene glycol | 5.00 |
| Water QS | 100.00 |

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description or defined in the appended claims be interpreted as descriptive and illustrative of the invention. Many modifications and variations of the present invention are possible in light of the above teachings. It is therefore to be understood that within the scope of the appended claims, the invention may be practiced otherwise than as specifically described.

What is claimed is:

1. A stable viscous hair relaxer, waving or curling composition having hair conditioning activity comprising a mixture of at least one alkaline earth metal hydroxide that relaxes strands of hair; and a hair conditioning amount of at least one cationic guar, said cationic guar being stable in the composition over time, and a cosmetically acceptable vehicle therefor, said composition having a pH of 12 to 14, said cationic guar being a polygalactomannan comprising mannose and galactose having at least one quaternary ammonium compound reacted therewith, said quaternary ammonium compound having the structure:

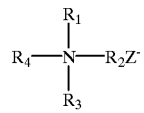

wherein $R_1$, $R_2$, and $R_3$ are alkyl, aryl and substituted alkyl and aryl groups; $R_4$ is selected from the group consisting of epoxyalkyl and halohydrin, and $Z^-$ is an anion.

2. The composition according to claim 1, wherein the alkaline earth metal hydroxide is selected from the group consisting of sodium hydroxide, lithium hydroxide, potassium hydroxide, barium hydroxide, strontium hydroxide, and mixtures thereof, provided that when the alkaline earth hydroxide is calcium hydroxide the composition further contains an activator.

3. The composition according to claim 1, wherein the alkaline earth metal hydroxide is present in an amount of about 1.5 to about 5% by weight based on the total weight of the composition.

4. The composition according to claim 1, wherein the pH of the composition is about 12 to about 13.5.

5. The composition according to claim 4, wherein the pH of the composition is about 12.5 to about 13.5.

6. The composition according to claim 1, wherein the cationic guar is a quaternary ammonium derivative of hydroxypropyl guar.

7. The composition according to claim 6, wherein the cationic guar is guar hydroxypropyltrimonium chloride.

8. The composition according to claim 1, wherein the cationic guar is present in the composition at about 0.5% to about 5.0%, by weight, based on the total weight of the composition.

9. The composition according to claim 1, wherein the relaxer component is an alkaline earth metal hydroxide selected from the group consisting of sodium hydroxide, calcium hydroxide, lithium hydroxide, potassium hydroxide, barium hydroxide, strontium hydroxide and mixtures thereof.

10. The composition according to claim 1, further comprising an auxiliary conditioning agent.

11. The composition according to claim 10, wherein the auxiliary conditioning agent is selected from the group consisting of quaternary ammonium compounds, amines, ethyl sulfates and cationic polymers.

12. The composition according to claim 11, wherein the auxiliary conditioning agent is polyquaternium 10 or behentrimonium methosulfate.

13. A composition for conditioning hair comprising a mixture of a cationic guar in an amount effective to impart a conditioning effect to the hair and a cosmetically acceptable vehicle therefor, said composition having a pH 12 to 14, said cationic guar being a polygalactomannan comprising mannose and galactose having at least one quaternary ammonium compound reacted therewith, said quaternary ammonium compound having the structure:

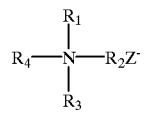

wherein $R_1$, $R_2$, and $R_3$ are alkyl, aryl and substituted alkyl and aryl groups; $R_4$ is selected from the group consisting of epoxyalkyl and halohydrin, and $Z^-$ is an anion.

14. The composition according to claim 13, wherein the pH is about 12 to about 13.5.

15. The composition according to claim 14, wherein the pH of the composition is about 12.5 to about 13.5.

16. The composition according to claim 13, wherein the cationic guar is a quaternary ammonium derivative of hydroxypropyl guar.

17. The composition according to claim 16, wherein the cationic guar is guar hydroxypropyltrimonium chloride.

18. The composition according to claim 13, wherein the cationic guar is present in the composition at about 0.5% to about 5.0%, by weight, based on the total weight of the composition.

* * * * *